United States Patent
Chou et al.

(10) Patent No.: US 8,133,750 B2
(45) Date of Patent: Mar. 13, 2012

(54) METHOD FOR FORMING EXTENDED GATE FIELD EFFECT TRANSISTOR (EGFET) BASED SENSOR AND THE SENSOR THEREFROM

(75) Inventors: Jung-Chuan Chou, Yunlin County (TW); Cheng-Wei Chen, Pingtung (TW); Yu-Huei Jiang, Miaoli County (TW)

(73) Assignee: National Yunlin University of Science and Technology, Yunlin (TW)

( * ) Notice: Subject to any disclaimer, the term of this patent is extended or adjusted under 35 U.S.C. 154(b) by 594 days.

(21) Appl. No.: 12/343,252

(22) Filed: Dec. 23, 2008

(65) Prior Publication Data
US 2009/0278175 A1    Nov. 12, 2009

(30) Foreign Application Priority Data
May 8, 2008    (TW) .............................. 97116965 A

(51) Int. Cl.
*H01L 21/00*    (2006.01)

(52) U.S. Cl. ............ 438/49; 257/44; 257/414; 257/773; 257/E21.091

(58) Field of Classification Search ............... 257/44, 257/414, 428, 429, 607, 734, 773, E21.091; 438/48, 49, 56, 57, 407, 520, 528, 548, 918
See application file for complete search history.

(56) References Cited

U.S. PATENT DOCUMENTS

| | | | | |
|---|---|---|---|---|
| 5,320,735 | A * | 6/1994 | Kato et al. | 204/419 |
| 2004/0185591 | A1 * | 9/2004 | Hsiung et al. | 438/49 |
| 2007/0227884 | A1 * | 10/2007 | Chou et al. | 204/403.01 |
| 2009/0188407 | A1 * | 7/2009 | Karvinen | 106/286.3 |
| 2010/0187988 | A1 * | 7/2010 | Forrest et al. | 313/504 |
| 2011/0020582 | A1 * | 1/2011 | Kojima et al. | 428/64.5 |

* cited by examiner

*Primary Examiner* — Evan Pert
*Assistant Examiner* — Scott R Wilson

(57) ABSTRACT

The invention provides a method for forming an extended gate field effect transistor (EGFET) based sensor, including: (a) providing a substrate; (b) forming a sensing film including titanium dioxide, ruthenium doped titanium dioxide or ruthenium oxide on the substrate; and (c) forming a conductive wire extended from the sensing film for external contact.

33 Claims, 8 Drawing Sheets

METHOD FOR FORMING EXTENDED GATE FIELD EFFECT TRANSISTOR (EGFET) BASED SENSOR AND THE SENSOR THEREFROM

CROSS REFERENCE TO RELATED APPLICATIONS

This Application claims priority of Taiwan Patent Application No. 097116965, filed on May 8, 2008, the entirety of which is incorporated by reference herein.

BACKGROUND OF THE INVENTION

1. Field of the Invention

The present invention relates to a method for forming an extended gate field effect transistor (EGFET) based sensor, and in particular relates to a method for forming titanium dioxide, ruthenium doped titanium dioxide and ruthenium oxide sensing films.

2. Description of the Related Art

Titanium dioxide ($TiO_2$) material has advantages such as a high refractive index, a high dielectric constant, stable chemical properties, well insulation, high hardness, and wear-resistance, etc., and thus is usually applied in high refractive index films, gas sensor films and wet sensor films of optical interference multi-layer film filters, anti-reflection films and high reflection films, and microelectronics devices.

Ion sensitive field effect transistor (ISFET) is a product from the electrochemical field that is combined with semiconductor technology and has the advantage of scaling and is suitable for automatic measurement. ISFET has ion sensitive functions and field effect transistor properties. Therefore, ISFETs are different from traditional ion-selective electrodes (ISE). In comparison with traditional glass electrodes, an ISFET has advantages of cable of scaling and measuring trace amounts of a solution, high input impedance, low output impedance, being a good generalized impedance converter, fast response time, process compatibility with a MOSFET, manufacturing ease, and being applied in development of biosensors, etc.

Extended gate field effect transistors (EGFET) are developed from ISFET devices and the cost thereof is low and structure thereof is simple. EGFETs can solve the packaging problem of ISFETs. EGFETs stabilize the metal gate when MOSFETs are being formed and separate the sensing film from the gate of the field effect transistor, wherein the sensing film and the gate of the field effect transistor are connected by a signal wire. The binding behaviors of the ion sensing films of ISFETs and EGFETs are the same and the difference between ISFETs and EGFETs is that ISFETs need an insulation film having high resistivity and high dielectric constant while EGFETs transfer the interfacial potential formed from the ion sensing film by a signal wire, and thus a conductive film with low resistivity is needed to transfer the potential.

Traditional ISFETs and EGFETs are only used to measure the hydrogen ion concentration of a solution. If a sensing film is coated with a specific enzyme, the enzyme film will interact with a specific substrate in the solution and result in hydrogen ions changing the interfacial potential of the sensing film. Then, the changed hydrogen ion concentration of the solution is measured by and ISFET and EGFET to detect the concentration of the specific substrate in the solution. The ISFET and EGFET mentioned above are called enzyme field effect transistors (ENFETs).

Ion-selective electrodes and biosensors are combined with molecular biology and electronic technologies, to develop electrical instruments and measurement products related to medical treatments. According to the definition from the National Academies, biosensors are integrated extensive products of molecular activity or active systems, which are applied to sensing devices and measurement systems such as enzyme molecules or protein antibodies. The measuring instruments are provided to detect relative specific substances in the environment. Bio-chip measurement systems belong to one of the biosensor system, which not only monitors and detects organisms and physiological parameters for real time or a long time study, but also is applied to detect contents of foods and the environment.

U.S. Pat. No. 4,877,582 discloses a chemical sensor having a field-effect transistor as an electronic transducer that is used for the analysis of specific constituents in a liquid. The chemical sensor comprises means for which an externally supplied sample solution is permitted to reach a chemical receptor of the chemical sensor while substantially preventing external light from reaching the field effect transistor. U.S. Pat. No. 6,218,208 discloses a sensitive material-tin oxide ($S_nO_2$) obtained by thermal evaporation or by r.f. Reactive sputtering process is used as a high-pH-sensitive material for a Multi-Structure Ion Sensitive Field Effect Transistor. The multi-structure of this Ion Sensitive Field Effect Transistor (ISFET) includes a $S_nO_2/SiO_2$ gate ISFET or $S_nO_2/Si_3N_4/SiO_2$ gate ISFET respectively, which has high performances such as a linear pH sensitivity of approximately 56-58 mV/pH in a concentration range between pH 2 and pH 10. Meanwhile, a low drift characteristic is approximately 5 mV/day and response time is less than 0.1 second. U.S. Pat. No. 6,251,246 discloses a polymeric material, wherein a stable and reproducible interface is between ionic and electronic domains of an ion selective sensor, or an ion selective field effect transistor, or the like is provided. When employed in an ion selective sensor, the polymeric material is advantageously provided over a solid internal reference electrode and an ion selective material is provided thereover. U.S. Pat. No. 4,992,382 discloses a method for measuring calcium ions, wherein a calcium sensitive reagent, calcichrome, is immobilized on a porous polymer film. The reaction of the calcium sensitive reagent to the $Ca^{2+}$ is then measured and concentration determined as a function of the reaction.

U.S. Pat. No. 4,946,574 discloses an apparatus for the production of sterilized calcium-ion water, which includes a housing structure and an electrolytic cell with electrical terminals and electrodes installed in the housing structure. A plurality of electromagnetic valves separately provided at a water-intake pipe and a water-drain pipe communicates with the electrolytic cell. A setting switch is disposed in the housing structure and is electrically coupled with the electrolytic cell for adjusting the current intensity of electrolysis therewith. A hydraulic-pressure switch is provided at a water pressure pipe for the control of the water-level in the electrolytic cell. Moreover, an ultraviolet sterilizing tank is connected to the electrolytic cell for sterilizing the electrolyzed water. Meanwhile, a control circuit is used to respectively couple with the electrolytic cell, the electromagnetic valves and the setting and hydraulic switches, whereby, calcium-ion water can be effectively produced for drinking purposes. US Patent Publication No. 20060008915 A1 discloses a method for determination of calcium in a sample derived from a living body, by the reaction of calcium in the sample with Chlorophosphonazo-III or a compound analogous thereto in the presence of vanadate ions. Calcium in the sample is determined on the basis of an optical change caused by the reaction product. Following are advantageous of the disclosed. The disclosure eliminates the problem of absorption of carbonic acid gas caused by a high pH and the problem of using a toxic reagent containing arsenic. Additionally, the disclosure makes it possible to test a large number of samples in short period of time due to use of an autoanalyzer. Furthermore, calcium determination of a wide range is permitted because of low sample blank values of the disclosure.

U.S. Pat. No. 5,102,527 discloses a calcium ion selective electrode having a sensitive membrane comprising an organic polymeric substance, a plasticizer and a calcium ion sensitive substance of a neutral carrier type, wherein the dielectric constant of the plasticizer is 10 or less, thus remarkably improving the responsiveness and stability of the electrode. U.S. Pat. No. 5,496,522 discloses a chemical sensor and biosensor probes for measuring low concentration of metals and metal ions in complex samples such as biological fluids, living cells, and environmental samples. The disclosure relates to a gel-based Indo-1 and Fura-2 chemical sensor probes for the measurement of low concentrations of calcium, cadmium, magnesium and the like.

BRIEF SUMMARY OF THE INVENTION

The invention provides a method for forming an extended gate field effect transistor (EGFET) based sensor, comprising: (a) providing a substrate; (b) forming a sensing film comprising titanium dioxide, ruthenium doped titanium dioxide or ruthenium oxide on the substrate; and (c) forming a conductive wire extended from the sensing film for external contact.

The invention also provides an extended gate field effect transistor based sensor, comprising: a substrate; a sensing film comprising titanium dioxide, ruthenium doped titanium dioxide or ruthenium oxide on the substrate; and a conducting wire extended from the sensing film as an electrical contact.

The invention further provides an extended gate field effect transistor based sensor, comprising: a substrate; a sensing film comprising titanium dioxide, ruthenium doped titanium dioxide or ruthenium oxide on the substrate; a conducting wire extended from the sensing film as an electrical contact; and a calcium ion sensing membrane on the sensing film.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
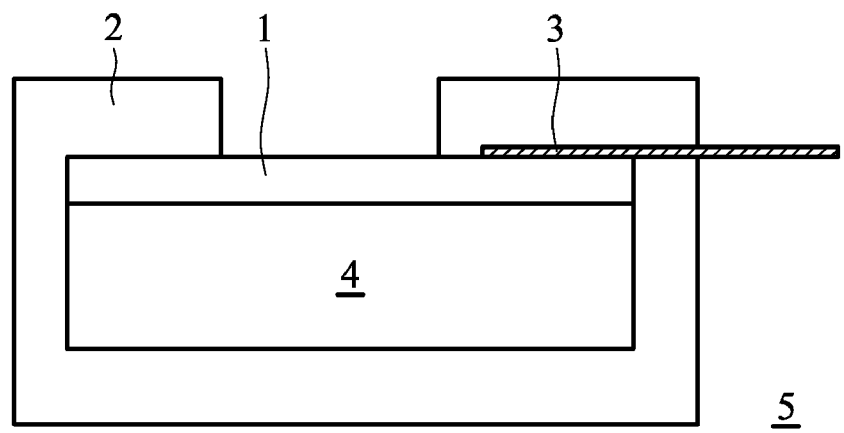
FIG. 1 shows a structural illustration of a sensor device of one embodiment of the invention.

The invention provides a method for forming an extended gate field effect transistor (EGFET) based sensor. As FIG. 1 shown, in one embodiment, the method for forming the sensor comprises first providing a substrate 4, wherein the substrate 4 may comprises a p-type silicon substrate or an n-type silicon substrate.

Then, a sensing film 1 comprising titanium dioxide, ruthenium doped titanium dioxide or ruthenium oxide is formed on the substrate 4. If the sensing film 1 comprises titanium dioxide or ruthenium oxide, the method for forming thereof may comprise a radio frequency sputtering process. A titanium dioxide target with purity greater than 99.99% is used in the radio frequency sputtering process for forming the sensing film comprising titanium dioxide, and a ruthenium target with purity greater than 99.99% is used in the radio frequency sputtering process for forming the sensing film 1 comprising ruthenium oxide. Power of the radio frequency sputtering process mentioned above is about 100-150 W, preferably 100 W. If the sensing film 1 comprises ruthenium doped titanium dioxide, the method for forming thereof may comprise a co-sputtering process, wherein the co-sputtering process comprises simultaneously performing a radio frequency sputtering process and DC sputtering process. A titanium dioxide target with purity greater than 99.99% and a ruthenium target with purity greater than 99.99% may be used in the co-sputtering process mentioned above. Power of the radio frequency sputtering process is about 100-120 W, preferably 100 W, and power of the DC sputtering process is about 30-40 W, preferably 30 W.

A processing time for the radio frequency sputtering process for forming the sensing film 1 comprising titanium dioxide is about 1 hour-1.5 hours, preferably 1 hour. Moreover, a processing time for the radio frequency sputtering process for forming the sensing film 1 comprising ruthenium oxide is about 10 minutes-1 hour, preferably 15 minutes. Furthermore, a processing time for the co-sputtering process for forming the sensing film 1 comprising ruthenium doped titanium dioxide is about 1 hour-1.5 hours, preferably 1 hour.

If the sensing film 1 comprises titanium dioxide or ruthenium doped titanium dioxide, a deposition pressure for forming the sensing film 1 comprising titanium dioxide or ruthenium doped titanium dioxide is about 25-35 mTorr, preferably 30 mTorr. An argon gas flow for forming the sensing film 1 comprising titanium dioxide or ruthenium doped titanium dioxide is about 35-50 sccm, preferably 40 sccm, and an oxygen gas flow for forming the sensing film 1 comprising titanium dioxide or ruthenium doped titanium dioxide is about 2-5 sccm, preferably 2 sccm, wherein a ratio of the argon gas flow and the oxygen gas flow is about 7/1-25/1, preferably 20/1. If the sensing film 1 comprises ruthenium oxide, a deposition pressure for forming the sensing film 1 comprising ruthenium oxide is about 8-15 mTorr, preferably 10 mTorr. An argon gas flow for forming the sensing film 1 comprising ruthenium oxide is about 35-50 sccm, preferably 40 sccm, and an oxygen gas flow for forming the sensing film 1 comprising titanium dioxide or ruthenium doped titanium dioxide is about 12-25 sccm, preferably 20 sccm, wherein a ratio of the argon gas flow and the oxygen gas flow is about 5/3-10/3, preferably 2/1. Furthermore, the resulting sensing film 1 comprising ruthenium doped titanium dioxide has a surface crystal size of about 37-61 nm.

Then, a conductive wire 3 is formed extended from the sensing film 1 for external contact to complete a sensor 5 of the invention. A material of the conductive wire 3 may comprise copper or aluminum. A sensitivity of the resulting extended gate field effect transistor based sensor is about 48-60 mV/pH from pH 1 to pH 13.

A package material 2 may be further used to package the sensor of the invention, wherein the package material 2 may comprise epoxy resin. As FIG. 1 shows, the sensor 5 of the invention comprises a substrate 4, a sensing film 1 comprising titanium dioxide, ruthenium doped titanium dioxide or ruthenium oxide on the substrate 4, a conductive wire 3 extended from the sensing film and a package material 2 packaging the entire sensor device 5.

Figure 2:
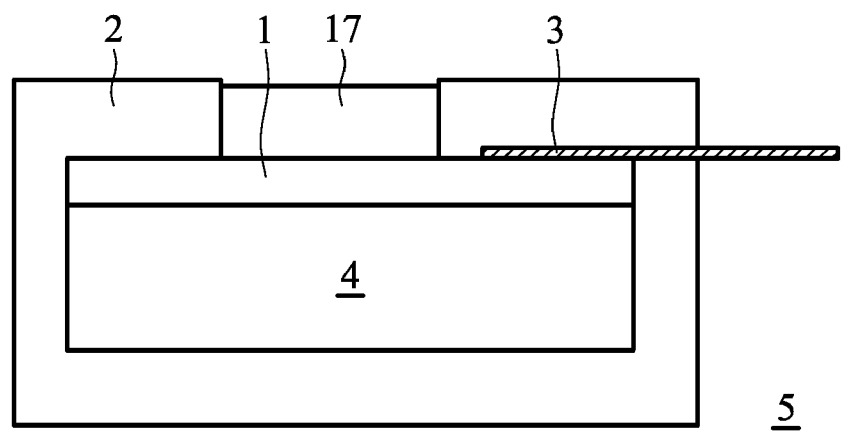
FIG. 2 is shows a structural illustration of a sensor device of another embodiment of the invention.

As FIG. 2 shows, in another embodiment of the invention, as mentioned above, after the conductive wire 3 is formed, a calcium ion sensing membrane 17 is further formed on the sensing film 1 comprising titanium dioxide, ruthenium doped titanium dioxide or ruthenium oxide to form a calcium ion sensor device 5 used for detecting calcium ions.

A material for forming the calcium ion sensing membrane 17 may comprise a polymeric material, a plasticizing agent, an ion selective material, and an anionic and potassium ion complex material, wherein a ratio of the polymeric material, plasticizing agent, ion selective material, and anionic and potassium ion complex material is about 54.9-59.4:38.5-39.5:1-2:0.6-2. The materials mentioned above is added to a solvent and mixed to form a mixture, wherein an amount of the solvent preferable is 1-5 ml. Then, the mixture is added on the sensing film 1 comprising titanium dioxide, ruthenium doped titanium dioxide or ruthenium oxide and after the solvent is evaporated, the calcium ion sensing membrane 17 is completed.

In addition, the polymeric material may comprise polymer vinyl chloride (PVC). The plasticizing agent comprises bis (2-ethylhe-xyl)sebacate (DOS). The ion selective material comprises calcimycin. The anionic and potassium ion complex material comprises potassium tetrakis(4-chlorophenyl) borate. The solvent comprises tetrahydrofuran.

A package material 2 may be further used to package the sensor of the invention, wherein the package material 2 may comprise epoxy resin. As FIG. 2 shows, the sensor device 5 of the invention comprises a substrate 4, a sensing film 1 comprising titanium dioxide, ruthenium doped titanium dioxide or ruthenium oxide on the substrate 4, a conductive wire 3 extended from the sensing film, a calcium ion sensing membrane 17 on the sensing film 1 and a package material 2 packaging the entire sensor 5.

EXAMPLE

1. Fabrication Processes for the Sensor Device Having the Sensing Film Comprising Titanium Dioxide A p-type silicon substrate was provided and a radio frequency sputtering process was performed on the p-type silicon substrate to form the sensing film comprising titanium dioxide. The parameters for the radio frequency sputtering process were as follows.

Power of the radio frequency sputtering process was 100 W and a deposition pressure of the radio frequency sputtering process was 30 mTorr. Purity of the titanium dioxide target used in the radio frequency sputtering process was 99.99%. In the processing, argon gas flow was 40 sccm, and an oxygen gas flow was 2 sccm. The processing time was 1 hour.

Then, a conductive wire was formed extended from the sensing film for external contact.

Finally, the sensor device was packaged with epoxy resin.

2. Fabrication Processes for the Sensor Device Having the Sensing Film Comprising Ruthenium Doped Titanium Dioxide A p-type silicon substrate was provided and a co-sputtering process (the co-sputtering process system is composed of a radio frequency sputtering process source and DC sputtering process source) was performed on the p-type silicon substrate to form the sensing film comprising titanium dioxide. The parameters for the co-sputtering process were as follows.

A radio frequency sputtering process and a DC sputtering process were simultaneously performed to reach the effect of trace doping. Power of the radio frequency sputtering process was 100 W and power of the DC sputtering process was 30 W. A deposition pressure of the co-sputtering process was 30 mTorr. Purity of the titanium dioxide target used in the co-sputtering process was 99.99% and purity of the ruthenium target used in the co-sputtering process was 99.99%. In the processing, an argon gas flow was 40 sccm and an oxygen gas flow was 2 sccm. The processing time was 1 hour.

Then, a conductive wire was formed extended from the sensing film for external contact.

Finally, the sensor device was packaged with epoxy resin.

3. Fabrication Processes for the Sensor Device Having the Sensing Film Comprising Ruthenium Oxide A p-type silicon substrate was provided and a radio frequency sputtering process was performed on the p-type silicon substrate to form the sensing film comprising titanium dioxide. The parameters for the radio frequency sputtering process were as follows.

Power of the radio frequency sputtering process was 100 W and a deposition pressure of the radio frequency sputtering process was 10 mTorr. Purity of the ruthenium target used in the radio frequency sputtering process was 99.99%. In the processing, an argon gas flow was 40 sccm and an oxygen gas flow was 20 sccm. The processing time was 15 minutes.

Then, a conductive wire was formed extended from the sensing film for external contact.

Finally, the sensor device was packaged with epoxy resin.

4. Determination of the Surface Morphology of the Sensing Film

Figure 3:
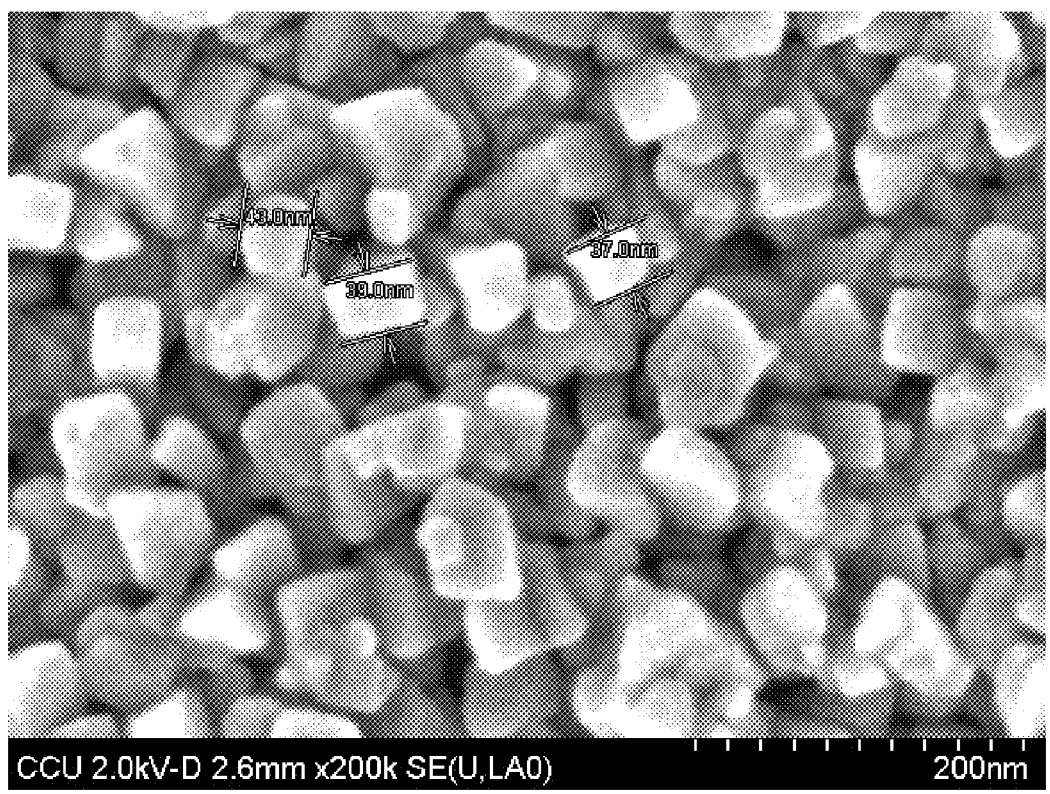
FIG. 3 shows the surface morphology of the ruthenium doped titanium dioxide film.

A Scanning Electron Microscopy (SEM) was used to observe the surface morphology of the sensing film comprising ruthenium doped titanium dioxide formed by the co-sputtering process in the invention, and the result was shown in FIG. 3. The result showed that in the preferable process, a surface crystal size of the sensing film comprising titanium dioxide was about 37-43 nm. Furthermore, in the appropriate process, a surface crystal size of the sensing film comprising titanium dioxide was about 37-61 nm.

5. Fabrication Processes for the Sensor Device of the Invention Having a Calcium Ion Sensing Membrane The polymeric material was used to prepare the ion selective membrane in the invention and the process was as follows.

In the process for forming the calcium ion sensing membrane of the invention, the polymeric material, polymer vinyl chloride (PVC), was added into the plasticizing agent, bis(2-ethylhe-xyl)sebacate (DOS) and the ion selective material ETH129 and anionic and potassium ion complex material-potassium tetrakis(4-chlorophenyl) borate, were added into tetrahydrofuran, respectively. Then, the polymer solution was oscillated by an ultrasonic cleaner. The detailed steps were as follows:

(1) PVC (0.549 g) and DOS (0.39 g) were mixed with tetrahydrofuran solvent solution (5 ml).

(2) The polymer solution obtained from step (1) was oscillated by an ultrasonic cleaner for 30 minutes, and then solution 1 was formed.

(3) ETH129 (25 mg) was mixed with tetrahydrofuran (1 ml).

(4) The solution obtained from step (3) was oscillated by an ultrasonic cleaner for 30 minutes, and then solution 2 was formed.

(5) Potassium tetrakis(4-chlorophenyl)borate (0.1 g) was mixed with tetrahydrofuran (1 ml).

(6) The solution obtained from step (5) was oscillated by an ultrasonic cleaner for 30 minutes, and then solution 3 was formed.

(7) The solution 1 (25 µl) and solution 2 (2 µl) were mixed with solution 3 (0.3 µl), and the mixture was oscillated by an ultrasonic cleaner for 30 minutes, and then the polymer solution for the first kind of sensing membrane was formed.

(8) The solution 1 (25 µl) and solution 2 (4 µl) were mixed with solution 3 (0.35 µl), and the mixture was oscillated by an ultrasonic cleaner for 30 minutes, and then the polymer solution for the second kind of sensing membrane was formed.

(9) The polymer solution for the first kind of sensing membrane was added on the sensing film comprising titanium dioxide of the sensor device having a sensing film comprising titanium dioxide mentioned above to form a first kind of sensor device having the calcium ion sensing membrane of the invention.

(10) The polymer solution for the second kind of sensing membrane was added on the sensing film comprising ruthenium oxide of the sensor device having a sensing film comprising ruthenium oxide mentioned above to form a second kind of sensor device having a calcium ion sensing membrane of the invention.

6. Current-Voltage (I-V) Measurement System

Figure 4:
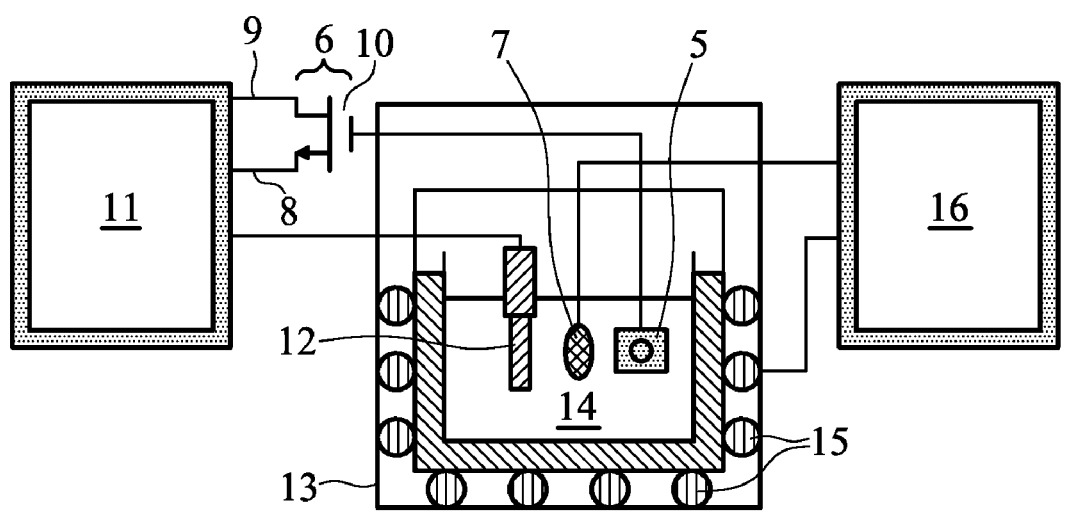
FIG. 4 shows an I-V measurement system of the invention.

The I-V measurement system used in the invention is shown in FIG. 4. The I-V curve of the sensor device was determined in a dark chamber 13 to prevent light from influencing the determined result for the I-V curve of the sensor 5. The source 8 and drain 9 and Ag/AgCl reference electrode 12 of the commercial IC (CD 4007 UB) (Toshiba) were connected to a test fixture and then connected to three semiconductor parameter analyzers 11 (Keithley 236), respectively to control the bias to let the MOSFET 6 work in the linear region. The test fixture was used to decrease the noise. The gate 10 was connected to the sensor 5. The heater 15 was used to raise the temperature and a proportional-integral and derivative (PID) 16 was used to stabilize the temperature to prevent inaccuracies due to temperature change. The parameters for Metrics software (Keithley) were set and the software was used to control relative signals. Furthermore, the sensor 5, thermocouple 7 and reference electrode 12 were dipped into the sample solution 14.

7. Hydrogen Ion Sensing Test

Sensitivity is one of the important parameters for a sensor device and the definition of sensitivity is that the surface charge of the interface between the solution and sensing film changes while each degree of the pH value changes. The test used the I-V measurement system mentioned above to measure pH values changes corresponding to the I-V curves of the sensor 5. In the I-V curve, when VDS was fixed, the output voltage would change with the pH value. Then, Microsoft Origin 7.0 software was used to analyze the data to obtain the sensitivity ($\Delta mV/\Delta pH$) of the sensor device of the invention.

Figure 5:
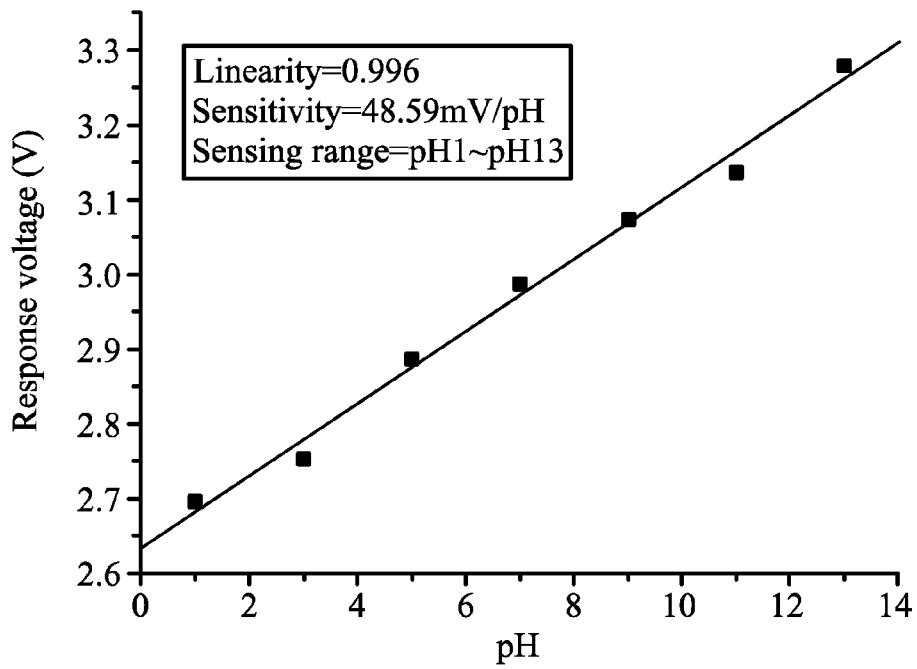
FIG. 5 shows the sensitivity and linearity of the sensor device having a titanium dioxide film.
Figure 6:
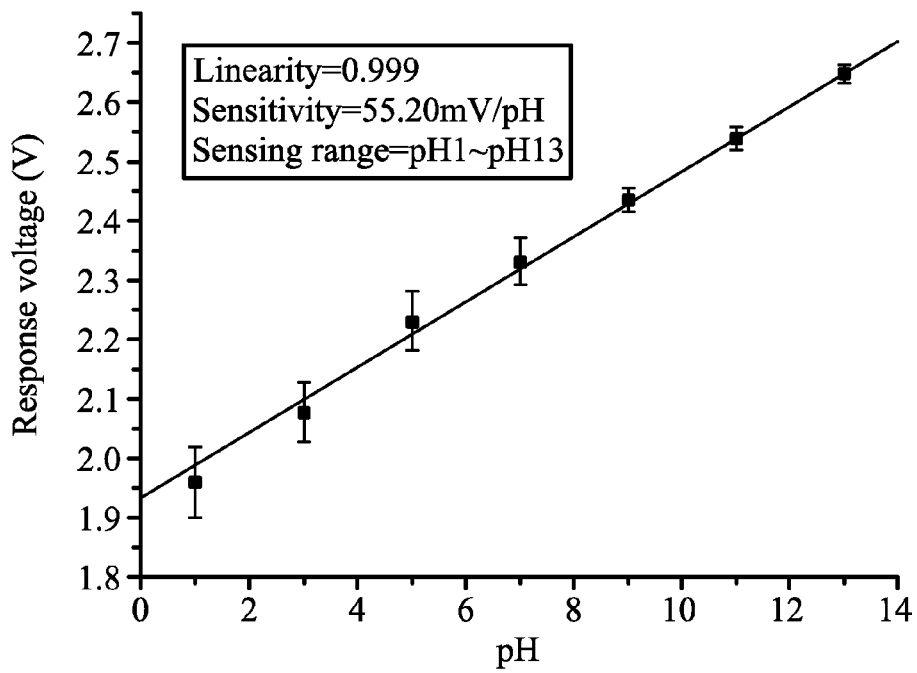
FIG. 6 shows the sensitivity and linearity of the sensor device having a ruthenium doped titanium dioxide film.
Figure 7:
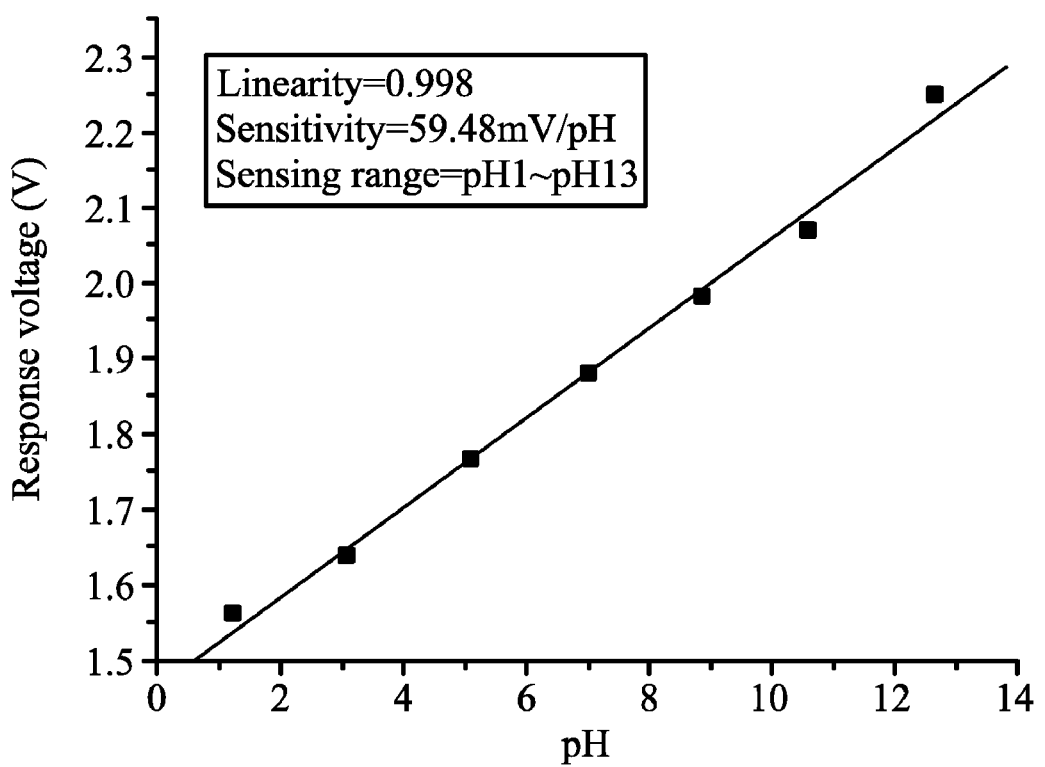
FIG. 7 shows the sensitivity and linearity of the sensor device having a ruthenium oxide film.

In the hydrogen ion sensing test, the sensor device having a sensing film comprising titanium dioxide was dipped in the buffer and combined with the Ag/AgCl reference electrode to perform the measurement. The result was shown in FIG. 5. The sensitivity and linearity of the sensor having a sensing film comprising titanium dioxide were 48.59 mV/pH and 0.996, respectively. The sensor having a sensing film comprising ruthenium doped titanium dioxide was dipped in the buffer and combined with the Ag/AgCl reference electrode to perform the measurement. The result was shown in FIG. 6. The sensitivity and linearity of the sensor having a sensing film comprising ruthenium doped titanium dioxide were 55.20 mV/pH and 0.999, respectively. The sensor having a sensing film comprising ruthenium oxide was dipped in the buffer and combined with the Ag/AgCl reference electrode to perform the measurement. The result was shown in FIG. 7. The sensitivity and linearity of the sensor device having a sensing film comprising ruthenium oxide were 59.48 mV/pH and 0.998, respectively. The sensing region of all sensors mentioned above was pH 1-pH 13.

8. Calcium Ion Sensing Test

In this test, two kinds of the sensors having the calcium ion sensing membrane mentioned above were used. One had the structure of the calcium ion sensing membrane/ruthenium doped titanium dioxide film/silicon substrate, and another had the structure of calcium ion sensing membrane/ruthenium oxide film/silicon substrate.

The test used the I-V measurement system mentioned above to measure the pCa changes corresponding to the I-V curve of the sensor device. In the I-V curve, when VDS was fixed the output voltage would change with the pCa value. Then, Microsoft Origin 7.0 software was used to analyze the data to obtain the sensitivity ($\Delta mV/\Delta pCa$) of the sensor device of the invention.

Preparation of the Calcium Ion Sample Solution

Five calcium ion sample solutions were prepared, and the concentrations thereof were 1 mol/L (pCa 0), $10^{-1}$ mol/L (pCa 1), $10^{-2}$ mol/L (pCa 2), $10^{-3}$ mol/L (pCa 3) and $10^{-4}$ mol/L (pCa 4), respectively. The detailed steps performed were as follows:

(1) Calcium ion sample solution with a concentration of pCa 0 was prepared. 7.351 g of $CaCl_2$ was added into 50 ml of D.I. water and the solution was stirred by a stir bar. Then 45 ml of the solution was taken as the calcium ion sample solution with a concentration of pCa 0.

(2) The remaining 5 ml of the solution was added into 45 ml of D.I. water and the solution was stirred by a stir bar. Then 45 ml of the solution was taken as the calcium ion sample solution with a concentration of pCa 1.

The diluted method mentioned above was used and than calcium ion sample solutions with concentrations of pCa 0, pCa 1, pCa 2, pCa 3 and pCa 4 were obtained, respectively.

Figure 8:
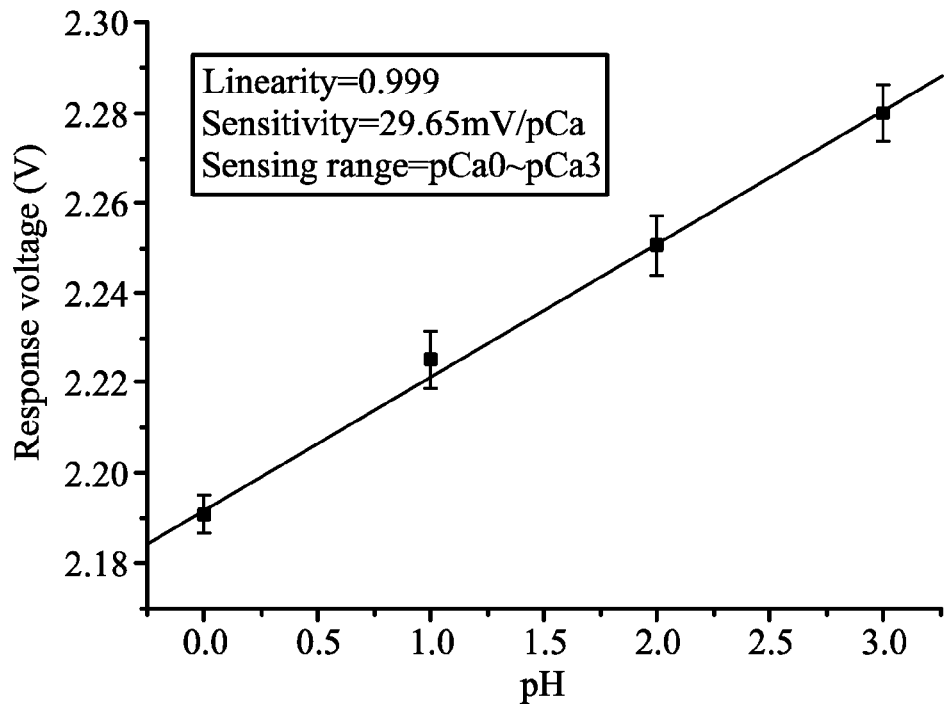
FIG. 8 shows the sensitivity and linearity of the sensor device having a calcium ion sensing membrane/ruthenium doped titanium dioxide film/silicon substrate structure.

In the calcium ion sensing test, the calcium ion sensor device of the invention was dipped in the calcium ion sample solutions with different concentrations and combined with the Ag/AgCl reference electrode to perform a measurement. The measurement result for the sensor having the structure of calcium ion sensing membrane/ruthenium doped titanium dioxide film/silicon substrate was shown in FIG. 8, wherein the sensitivity and linearity of the sensor device were 29.65 mV/pCa and 0.999, respectively and the sensing region thereof was pCa 0-pCa 3.

Figure 9:
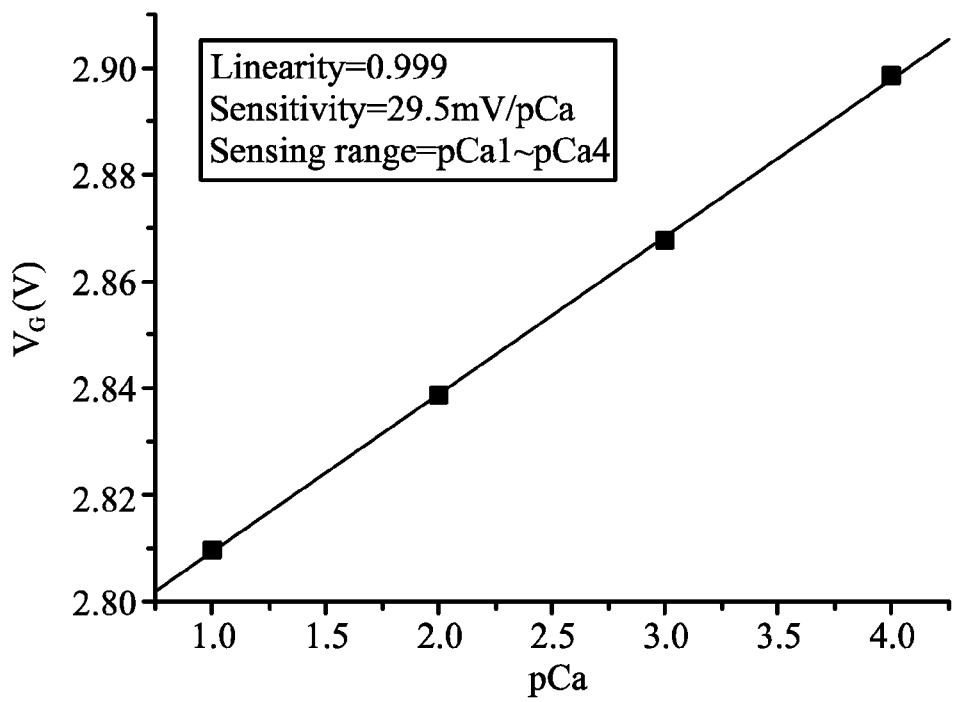
FIG. 9 shows the sensitivity and linearity of the sensor device having a calcium ion sensing membrane/ruthenium oxide film/silicon substrate structure.

The measurement result for the sensor having the structure of calcium ion sensing membrane/ruthenium oxide film/silicon substrate was shown in FIG. 9, wherein the sensitivity and linearity of the sensor device were 29.5 mV/pCa and 0.999, respectively and the sensing region thereof was pCab 1-pCa 4.

Figure 10:
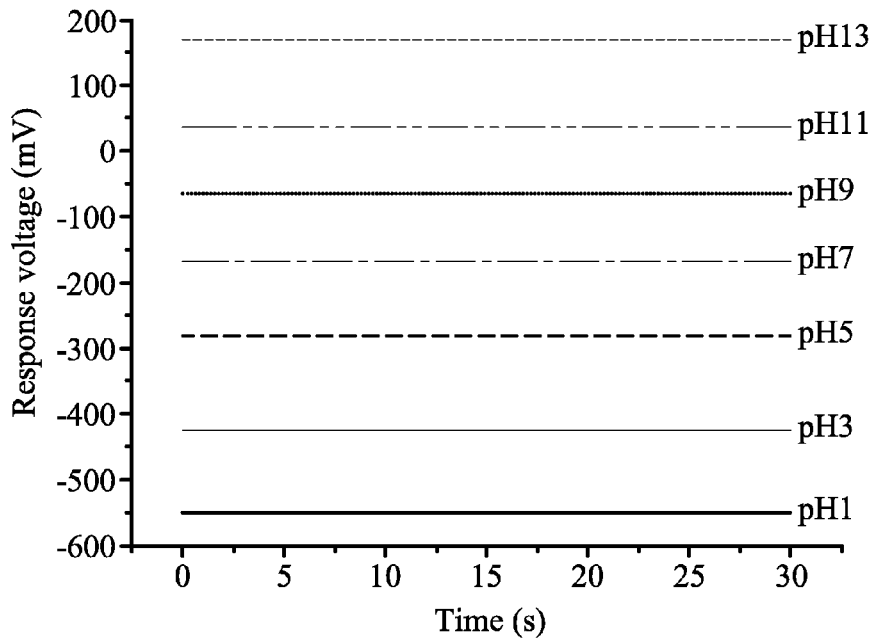
FIG. 10 shows voltage response curves of ruthenium doped titanium dioxide film for different pH buffer solutions.

9. Curve of Response Voltage-Time of the Sensing Film Comprising Ruthenium Doped Titanium Dioxide The sensor of the invention having a ruthenium doped titanium dioxide film was dipped into different sample solutions to perform measurements by a voltage-time measurement system. In the different sample solutions with different pH values, the ruthenium doped titanium dioxide film resulted in different response voltages, and the curves of response voltage-time thereof were shown in FIG. 10, wherein the sensing region thereof was pH 1-pH 13.

Figure 11:
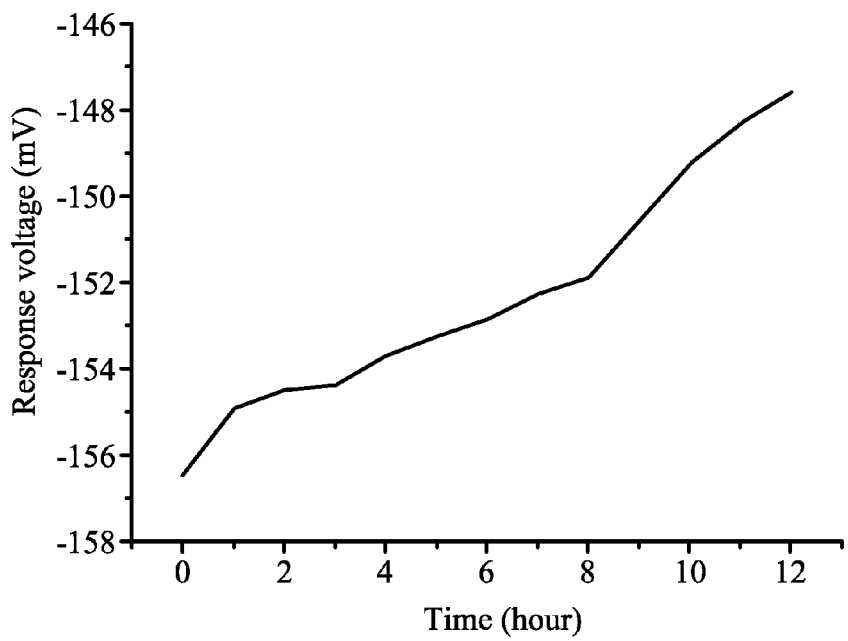
FIG. 11 shows a long-term drift curve of a ruthenium doped titanium dioxide film for pH 7 buffer solutions.

The ruthenium doped titanium dioxide film of the invention dipped in the same sample solution resulted in a response voltage which changed over time, which was due to drift effect. The ruthenium doped titanium dioxide film of the invention dipped in a pH 7 solution for 12 hours and the curve of the response voltage-time thereof was shown FIG. 11, wherein drift rate thereof was 0.745 mV/hour.

Figure 12:
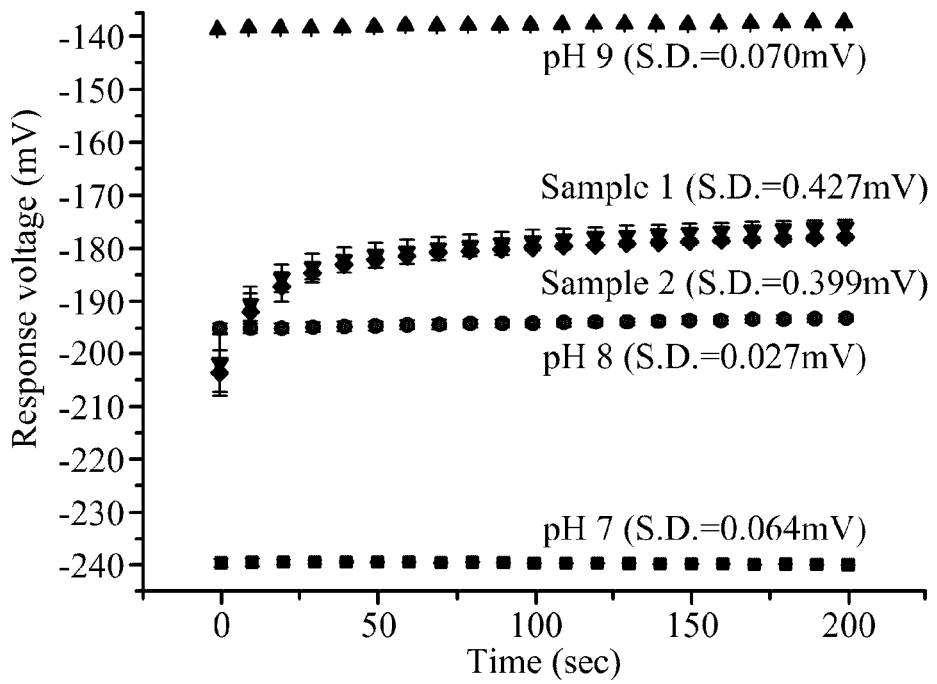
FIG. 12 shows response time of an EGFET sensor having a ruthenium doped titanium dioxide film in hard clam cultivated solutions.

Response time of the EGFET sensor having a ruthenium doped titanium dioxide film in pH standard buffer solution from pH 1-pH 13 was all shorter then 1 second. However, a larger response time was found for of an EGFET sensor having a ruthenium doped titanium dioxide film in hard clam cultivated solutions, as shown in FIG. 12. In order to provide for a based reference level and potential calibration, the EGFET sensor having a ruthenium doped titanium dioxide film sensor was immersed in pH 7, pH 8 and pH 9 for pH standard solutions and measured for 200 seconds. The mean response voltages and standard deviations were −240.37 mV (S.D.=0.064 mV), −194.566 mV (S.D.=0.027 mV) and −138.195 mV (S.D.=0.070 mV), respectively.

Figure 13:
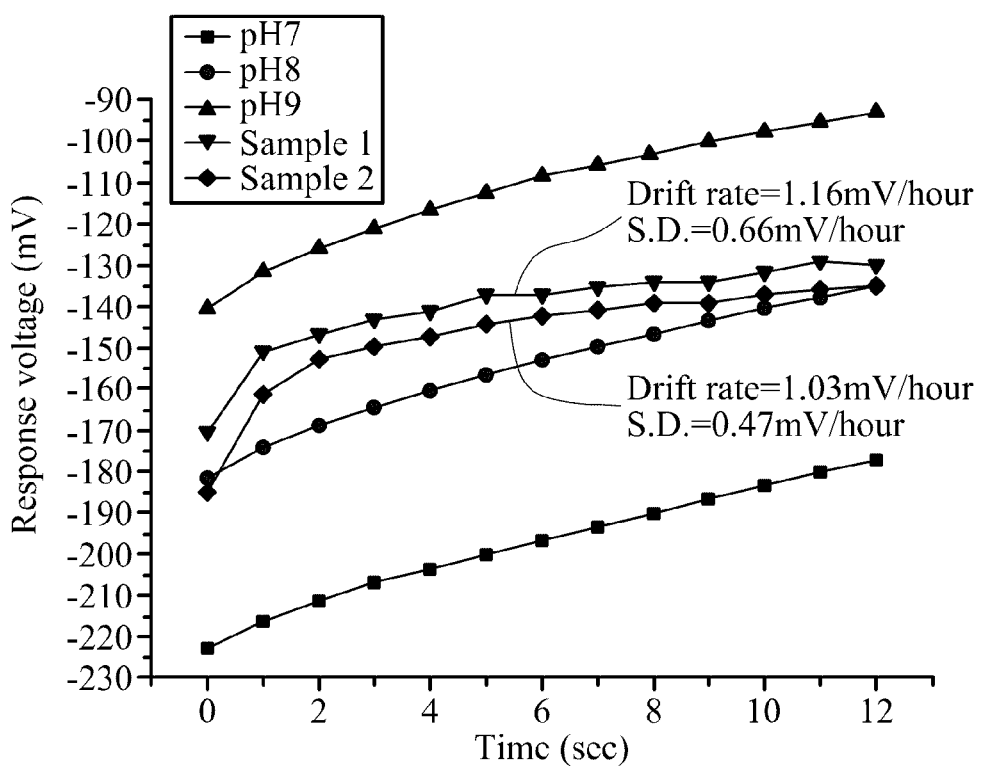
FIG. 13 shows long-term drift measurements of pH standard buffer solutions from pH 7 to pH 9 and cultivated solutions for the EGFET sensor having a ruthenium doped titanium dioxide film.

Long-term drift measurements of pH standard buffer solutions from pH 7 to pH 9 and cultivated solutions for the EGFET sensor having a ruthenium doped titanium dioxide film are exhibited in FIG. 13. According to the experimental results, drift rates and standard deviations from 5 hours to 12 hours for cultivated solutions (sample 1 and sample 2) were 1.16 mV/hour (S.D.=0.660 mV/hour) and 1.03 mV/hour (S.D.=0.473 mV/hour), respectively.

A hard clam cultivated solution was collected from cultivated ponds in Taishi (Yunlin country in Taiwan).

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for forming an extended gate field effect transistor (EGFET) based sensor, comprising:
   (a) providing a substrate;
   (b) forming a sensing film comprising titanium dioxide, ruthenium doped titanium dioxide or ruthenium oxide on the substrate;
   (c) forming a conductive wire extended from the sensing film for external contact; and
   (d) forming a calcium ion sensing membrane on the sensing.

2. The method for forming an extended gate field effect transistor based sensor as claimed in claim 1, wherein the substrate comprises an n-type silicon substrate or a p-type silicon substrate.

3. The method for forming an extended gate field effect transistor based sensor as claimed in claim 1, wherein a method for forming the sensing film comprising titanium dioxide or ruthenium oxide comprises a radio frequency sputtering process.

4. The method for forming an extended gate field effect transistor based sensor as claimed in claim 3, wherein a titanium dioxide target with purity greater than 99.99% is used in the radio frequency sputtering process for forming the sensing film comprising titanium dioxide, and a ruthenium target with purity greater than 99.99% is used in the radio frequency sputtering process for forming the sensing film comprising ruthenium oxide.

5. The method for forming an extended gate field effect transistor based sensor as claimed in claim 3, wherein power of the radio frequency sputtering process is about 100-150 W.

6. The method for forming an extended gate field effect transistor based sensor as claimed in claim 3, wherein a processing time for the radio frequency sputtering process for forming the sensing film comprising titanium dioxide is about 1 hour-1.5 hours.

7. The method for forming an extended gate field effect transistor based sensor as claimed in claim 3, wherein a processing time for the radio frequency sputtering process for forming the sensing film comprising ruthenium oxide is about 10 minutes-1 hour.

8. The method for forming an extended gate field effect transistor based sensor as claimed in claim 1, wherein a method for forming the sensing film comprising ruthenium doped titanium dioxide comprises a co-sputtering process.

9. The method for forming an extended gate field effect transistor based sensor as claimed in claim 8, wherein the co-sputtering process comprises simultaneously performing a radio frequency sputtering process and DC sputtering process.

10. The method for forming an extended gate field effect transistor based sensor as claimed in claim 9, wherein power of the radio frequency sputtering process is about 100-120 W and power of the DC sputtering process is about 30-40 W.

11. The method for forming an extended gate field effect transistor based sensor as claimed in claim 8, wherein a titanium dioxide target with purity greater than 99.99% and a ruthenium target with purity greater than 99.99% are used in the co-sputtering process.

12. The method for forming an extended gate field effect transistor based sensor as claimed in claim 8, wherein a processing time for the co-sputtering process is about 1 hour-1.5 hours.

13. The method for forming an extended gate field effect transistor based sensor as claimed in claim 1, wherein a deposition pressure for forming the sensing film comprising titanium dioxide or ruthenium doped titanium dioxide is about 25-35 mTorr.

14. The method for forming an extended gate field effect transistor based sensor as claimed in claim 1, wherein a deposition pressure for forming the sensing film comprising ruthenium oxide is about 8-15 mTorr.

15. The method for forming an extended gate field effect transistor based sensor as claimed in claim 1, wherein an argon gas flow and an oxygen gas flow for forming the sensing film comprising titanium dioxide or ruthenium doped titanium dioxide are about 35-50 sccm and 2-5 sccm, respectively.

16. The method for forming an extended gate field effect transistor based sensor as claimed in claim 15, wherein a ratio of the argon gas flow and the oxygen gas flow is about 7/1-25/1.

17. The method for forming an extended gate field effect transistor based sensor as claimed in claim 1, wherein an argon gas flow and an oxygen gas flow for forming the sensing film comprising titanium dioxide or ruthenium doped titanium dioxide are about 40 sccm and 2 sccm, respectively.

18. The method for forming an extended gate field effect transistor based sensor as claimed in claim 17, wherein a ratio of the argon gas flow and the oxygen gas flow is about 20/1.

19. The method for forming an extended gate field effect transistor based sensor as claimed in claim 1, wherein an argon gas flow and an oxygen gas flow for forming the sensing film comprising ruthenium oxide are about 35-50 sccm and 15-25 sccm, respectively.

20. The method for forming an extended gate field effect transistor based sensor as claimed in claim 19, wherein a ratio of the argon gas flow and the oxygen gas flow is about 5/3-10/3.

21. The method for forming an extended gate field effect transistor based sensor as claimed in claim 1, wherein an argon gas flow and an oxygen gas flow for forming the sensing film comprising ruthenium oxide are about 40 sccm and 20 sccm, respectively.

22. The method for forming an extended gate field effect transistor based sensor as claimed in claim 21, wherein a ratio of the argon gas flow and the oxygen gas flow is about 2/1.

23. The method for forming an extended gate field effect transistor based sensor as claimed in claim 1, wherein a material for forming the calcium ion sensing membrane comprises a polymeric material, a plasticizing agent, an ion selective material and an anionic and potassium ion complex material.

24. The method for forming an extended gate field effect transistor based sensor as claimed in claim 23, wherein the material is added in a solvent.

25. The method for forming an extended gate field effect transistor based sensor as claimed in claim 24, wherein the solvent comprises tetrahydrofuran.

26. The method for forming an extended gate field effect transistor based sensor as claimed in claim 23, wherein a ratio of the polymeric material, plasticizing agent, ion selective material, and anionic and potassium ion complex material is about 54.9-59.4:38.5-39.5:1-2:0.6-2.

27. The method for forming an extended gate field effect transistor based sensor as claimed in claim 23, wherein the polymeric material comprises polymer vinyl chloride (PVC).

28. The method for forming an extended gate field effect transistor based sensor as claimed in claim 23, wherein the plasticizing agent comprises bis(2-ethylhe-xyl)sebacate (DOS).

29. The method for forming an extended gate field effect transistor based sensor as claimed in claim 23, wherein the ion selective material comprises calcimycin.

30. The method for forming an extended gate field effect transistor based sensor as claimed in claim 23, wherein the anionic and potassium ion complex material comprises potassium tetrakis(4-chlorophenyl) borate.

31. An extended gate field effect transistor based sensor, comprising:
a substrate;
a sensing film comprising titanium dioxide, ruthenium doped titanium dioxide or ruthenium oxide on the substrate;
a conducting wire extended from the sensing film as an electrical contact; and
a calcium ion sensing membrane on the sensing film.

32. The extended gate field effect transistor based sensor as claimed in claim 31, wherein a sensitivity of the extended gate field effect transistor based sensor is about 28-32 mV/pCa from pCa 0 to pCa 4.

33. The extended gate field effect transistor based sensor as claimed in claim 31, wherein a surface crystal size of the sensing film comprising titanium dioxide is about 37-61 nm.

* * * * *